United States Patent
Hickam et al.

[11] 3,977,232
[45] Aug. 31, 1976

[54] DIFFUSION-TYPE HYDROGEN METER

[75] Inventors: William M. Hickam, Pittsburgh; Robert E. Witkowski, West Mifflin; Edgar Berkey, Murrysville, all of Pa.

[73] Assignee: Westinghouse Electric Corporation, Pittsburgh, Pa.

[22] Filed: Mar. 30, 1972

[21] Appl. No.: 239,614

[52] U.S. Cl. .................................. 73/19; 176/19 R
[51] Int. Cl.² .......................................... G01N 7/10
[58] Field of Search .................... 73/19, 23, 194 R; 324/33; 176/19 E, 19 J, 19 R; 204/195 R, 195 S, 64 T

[56] References Cited
UNITED STATES PATENTS

| | | | |
|---|---|---|---|
| 1,911,853 | 5/1933 | Silcox | 73/194 R |
| 2,671,336 | 3/1954 | Hulsberg | 73/23 |
| 2,913,378 | 11/1959 | Dean et al. | 204/64 T |
| 3,463,004 | 8/1969 | Withnell | 73/194 R X |
| 3,498,900 | 3/1970 | Banks et al. | 324/33 X |
| 3,683,272 | 8/1972 | Vissers et al. | 73/19 X |
| 3,731,523 | 5/1973 | Vissers et al. | 73/23 X |

Primary Examiner—Richard C. Queisser
Assistant Examiner—Stephen A. Kreitman
Attorney, Agent, or Firm—M. P. Lynch

[57] ABSTRACT

A system for measuring and controlling the concentration of hydrogen in liquid sodium and in gaseous environments is disclosed. The system comprises a reinforced hollow tube-like membrane which is positioned in the sodium or the gaseous environment such that the hydrogen diffuses through the membrane. Hydrogen diffusing through the membrane is removed by an ion pump to maintain a vacuum inside the membrane. The electrical current flowing through the ion pump is an indication of the hydrogen concentration. Alternatively, the hydrogen can be permitted to diffuse through the membrane until an equilibrium condition is established and a high pressure ionization gauge can be used to determine the hydrogen concentration. The membrane includes integral reinforcing sections permitting the membrane to be thin to achieve high sensitivity and withstand a high differential pressure. Valves are included which isolate the membrane from the sodium or gaseous environment so that the membrane can be easily changed.

6 Claims, 4 Drawing Figures

DIFFUSION-TYPE HYDROGEN METER

BACKGROUND OF THE INVENTION

1. Field of the Invention

The invention relates to the measurement and control of gases and more particularly to the measurement and control of the hydrogen concentration in liquid and gaseous sodium.

2. Description of the Prior Art

Typical prior art diffusion type hydrogen measuring systems have utilized a thin membrane positioned in the sodium and a hydrogen detection system to measure the rate at which hydrogen diffused through the membrane. Typically, the membranes were formed from thin walled tubes of stainless steel or nickel with one end closed and the second end connected to the hydrogen detection system. The sensitivity of these systems was significantly influenced by the thickness of the membrane. Typical membranes were relatively thick because many applications required the membrane to be subjected to pressures in the range of 10 atmospheres and temperatures up to 1000°F.

Typically, the prior art membranes are positioned in the sodium stream and welded in place. This made changing the membrane without disturbing the sodium stream rather difficult if not impossible. This feature contributed significantly to the service problems of the system because the membranes must be changed when fouling of the surface of the membrane changes the rate of hydrogen diffusion through the membrane.

SUMMARY OF THE INVENTION

The disclosed invention substantially solves the above-described problems which were associated with the prior art systems. The disclosed systems utilize a thin tube-like membrane to significantly increase the sensitivity of the system. The membrane is closed at one end and is reinforced by either forming the membrane so that the walls of the membrane include thicker reinforcing portions or by selectively shaping the membrane such that the walls of the membrane are both thin and rigid. In either case the differential pressure to which a membrane of a given thickness may be safely subjected is substantially increased by the disclosed membrane design as compared to prior art membranes of the same thickness.

The membrane is positioned in a housing through which sodium or gas flows and is secured to the housing by a screw-type connector permitting the membrane to be easily removed. The membrane and the housing are positioned in a measurement loop which includes valves which permit the membrane to be isolated from the system utilizing the sodium. This permits the membrane to be easily replaced.

When the system is used to measure the hydrogen concentration in liquid sodium, the liquid sodium is permitted to freeze around the neck portion of the membrane to seal the system. An argon protective system is incorporated to protect the sodium for oxidation when the screw connection is removed to replace the membrane. An ion pump is used to measure the rate of hydrogen diffusion through the membrane. Provisions are also included for high pressure ionization gauge to permit the accuracy of the system to be checked by permitting hydrogen to diffuse through the membrane to achieve a steady state condition. Under these conditions, the high pressure ionization gauge is used to measure the hydrogen pressure on the inside of the membrane. Comparing this reading to the reading obtained by using the ion pump permits the contamination of the membrane to be checked and a new calibration established. It may be desirable to change the membrane if the calibration has changed more than a predetermined amount.

Although the preferred embodiment of the invention has been discussed above with reference to the measurement of hydrogen in sodium, the system is not so limited. The system may be used to measure the concentration of any gas including the hydrogen isotopes, deuterium and tritium which will preferentially diffuse through the membrane which is submerged in the liquid in which the gas is dissolved.

All the structural elements of the system are preferably made of either a nickel alloy or stainless steel thereby substantially solving the outgassing and corrosion problems associated with typical prior art systems.

DETAILED DESCRIPTION

Figure 1:
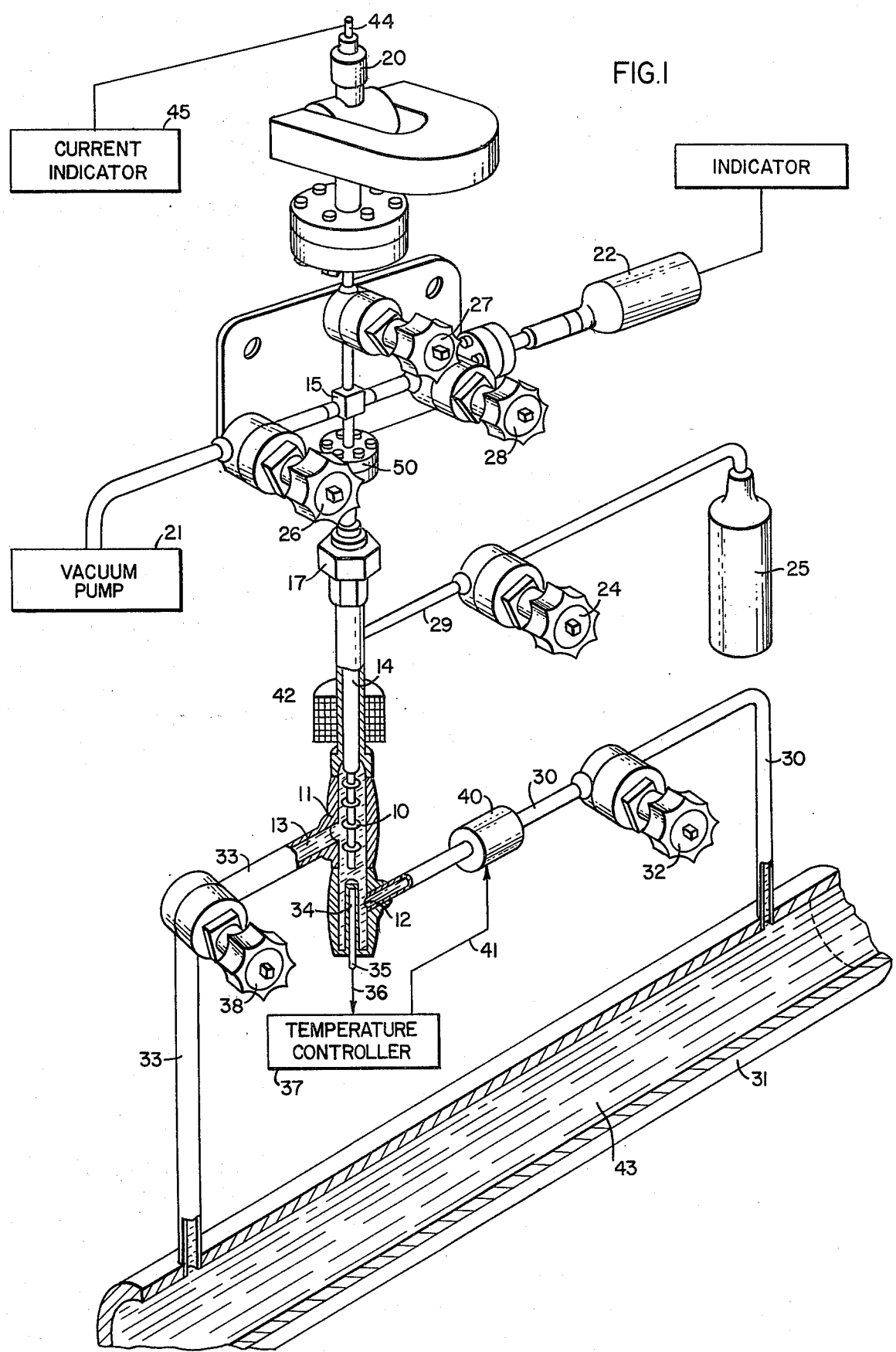
FIG. 1 is a pictorial diagram of the diffusion type hydrogen meter properly connected to measure the hydrogen concentration and liquid sodium.

FIG. 1 is a pictorial diagram of the diffusion type hydrogen meter which is the subject of this invention. The system includes a reinforced membrane 10 positioned in a housing 11. The housing 11 has two openings 12 and 13 which permit liquid sodium to enter the housing 11 and circulate around the reinforced membrane 10. The reinforced membrane 10 is connected to a tube 14 which is in turn secured to the housing 11 by mounting nut 17. The lower end of the reinforced membrane 10 is closed and the membrane 10 and the tube 14 are connected through a T connector 15 to an ion pump 20, a vacuum pump 21 and a high pressure ionization gauge 22. Three valves 26, 27 and 28 permit the vacuum pump 21, the ion pump 20 and the high pressure ionization gauge 22 to be selectively coupled to the reinforced membrane 10. The function of these components will be described in detail later.

The housing 11 has an opening 23 in the upper part thereof which is coupled through a tube 29 and valve 24 to a supply of compressed argon 25. A portion of the liquid sodium 43 flowing in conduit 31 enters the housing 11 via tube 30 and opening 12, circulates around the membrane 10, through the outlet opening 13 and returns to the conduit 31 via a tube 33. Tube 30 and 33 include valves 32 and 38. The reason for these valves will be discussed in detail later.

The housing 11 includes a sensor well 34 in the lower end thereof. A temperature sensor 35 is mounted in the sensor well 34 and coupled by a cable 36 to a temperature controller 37. The temperature controller 37 is in turn coupled to a heater element 40 by a cable 41. A second heater element 42 is positioned around the upper part of the housing 11.

The system illustrated in FIG. 1 is properly connected to measure the hydrogen content of liquid sodium, illustrated generally at reference numeral 43, which flows through the conduit 31. The system is placed in operation by evacuating membrane 10 by activating the vacuum pump 21. After the membrane 10 has been evacuated, a cut off valve 26 is closed to isolate the vacuum pump 21 from the membrane 10. The high pressure ionization gauge cut off valve 28 is also closed to isolate the high pressure ionization gauge 22 from the membrane 10 and the ion pump cut off valve 27 is opened to couple the ion pump 20 to the membrane 10. Liquid sodium is then pumped through conduit 31 such that a portion of the sodium flows through the housing 11 by way of the input tube 30 and the output tube 33. Should the application require such an arrangement, a pump (not illustrated) may be installed in the input tube 30 to assure that the desired amount of liquid sodium flows through the housing 11. The sodium flow through the housing 11 should be sufficient to assure that the sodium surrounding the membrane 10 has substantially the same hydrogen concentration as the sodium flowing through the conduit 31.

After the membrane 10 has been evacuated and the ion pump 20 connected to the membrane by opening the ion pump shut off valve 27, the ion pump 20 is started by coupling a high voltage to the ion pump electrode 44. The hydrogen in the sodium surrounding the membrane 10 diffuses through the membrane 10 and is removed by the ion pump 20. The current in the ion pump 20 has a predetermined relationship to the hydrogen removed from the space enclosed by the membrane 10 and the tube 14. The amount of hydrogen diffusing through the membrane 10 has a predetermined relationship to the concentration of hydrogen in the sodium surrounding the membrane 10. Thus, the current in the ion pump 20 is an indication of the hydrogen concentration in the sodium. The ion pump current is measured and displayed on a current indicator 45. The current indication may be visually observed or may be used to produce a control signal which may be coupled to other apparatus (not shown) to control the hydrogen concentration in the sodium or to perform other control functions. For example, the current in the ion pump 20 could be used to generate a signal which is coupled to apparatus to control the temperature of a cold trap which in turn controls the hydrogen concentration in the sodium.

A suitable ion pump is available commercially. A typical pump is Model No. 913-5000 manufactured by Varian Associates.

The rate at which hydrogen diffuses from the sodium through membrane 10 is a function of the concentration of hydrogen in the sodium and the temperature of the sodium. In order to eliminate the need for a correction for the temperature of the sodium it is normally preferred to maintain the temperature of the sodium surrounding the membrane 10 constant. In the illustrated system in FIG. 1 this is accomplished by positioning a temperature sensor 35 in the sensor well 34 to measure the temperature of the sodium in the vicinity of the membrane 10. The output of the temperature sensor 35 is coupled to a temperature controller 37 which is in turn coupled to a heater 40 which is positioned around the sodium input tube 30. The temperature controller 37 and the heater 40 are adjusted to maintain the temperature of the sodium entering the housing 11 substantially constant. This temperature is normally set higher than the temperature of the sodium flowing through the conduit 31. This simplifies the temperature control problem because it will always be necessary to add heat to the sodium flowing through the housing 11. This can be conveniently done by a simple resistance type heater positioned around the inlet tube 30.

An advantage of the system illustrated in FIG. 1 is that the membrane 10 can be easily changed without interrupting the system utilizing the liquid sodium flowing through the conduit 31. This is a particularly advantageous feature because the membrane 10 may become contaminated by deposits from the sodium. These deposits can materially affect the diffusion rate of the hydrogen through the membrane 10 thereby adversely affecting the calibration and sensitivity of the system.

In normal operation, the liquid sodium flowing through the housing 11 and around the membrane 10 is isolated from the outside environment by a coupling and nut 17. Further isolation of the sodium flowing around the membrane 10 from the outside environment is provided by a region of solidified sodium which naturally forms between the tube 14 and the housing 11. This solidified sodium forms when the valves 32 and 38 are opened to permit sodium to flow through the housing 11. Cooling means, such as fins, (not illustrated) may be required to cause this region of solidified sodium to form. The need for this cooling will depend on the temperature of the sodium and other system design details which effect heat dissipation.

To change the membrane 10, valves 32 and 38 are closed to assure that no sodium flows through the housing 11. Nut 17 is loosened and the argon cut off valve 24 is opened causing argon to flow through the opening 23 in the upper part of the housing 11. The argon completely covers the upper portion of the solidified sodium with an inert gas layer. A heating coil 42 positioned around the upper portion of the housing 11 is then activated to raise the temperature of the sodium in the housing 11 above its melting point. The sealing nut 17 is unscrewed from the housing 11 permitting the tube 14 and the membrane 10 secured thereto to be removed from the housing 11. During the time when the membrane 10 is removed from the housing a continuous stream of argon flows from the argon supply 25 into the housing 11 and escapes into the outside atmosphere. This flow of argon forms an inert layer of gas which protects the sodium from the atmosphere while the membrane 10 is being changed.

The membrane mounting tube is secured to one half of a high vacuum flange 50. The sections of the high vacuum flange 50 are disassembled and a new membrane assembly comprising a membrane and membrane mounting tube are secured to this flange and the mounting nut 17 tightened to secure the new membrane assembly in place. This completes the physical changing of the membrane and the system is returned to operation by activating the vacuum pump 21 to establish a vacuum inside the membrane and opening the valves 32 and 38 to permit sodium to flow through the housing 11. These operations were previously described in detail.

In applications where it is desirable the membrane 10 may be isolated from the sodium by an intermediate layer of a gas, such as argon, which will not diffuse through the membrane. In this configuration, the membrane 10 is submerged in the inert gas and the hydrogen diffuses out of the sodium, into the argon and through the membrane 10. The other operational details of the system are identical to those described above with reference to a system in which the membrane 10 was submerged in the liquid sodium.

A high pressure ionization gauge 22 is also coupled to the membrane 10 by a cut off valve 28. This gauge permits the membrane 10 to be checked for contamination which may effect the rate at which hydrogen diffuses through the membrane 10. The membrane 10 is checked for contamination by shutting off the ion vacuum pump 20 and permitting hydrogen to diffuse through the membrane 10 until a steady state condition is established. The pressure inside the membrane 10 during a steady state condition is a known function of the hydrogen concentration in the sodium. The contamination of the membrane 10 only effects the time necessary to establish the steady state condition. Once the steady state condition has been established the hydrogen pressure is measured using the high pressure ionization gauge 22. This reading is compared to the reading obtained by measuring the current in the ion pump 20. Any substantial difference between these two hydrogen measurements indicate that the membrane 10 is covered with deposits which adversely affect the accuracy of measurements made using the ion pump 20 and provides recalibration information which permits the continuous monitoring of true hydrogen levels. The high pressure ionization gauge 22 may be Model No. WL-23793 manufactured by Westinghouse.

The high pressure ionization gauge 22 can also be used to detect malfunctions in the ion pump 20. Including the ion pump 20 and the high pressure ionization gauge 22 in the systems permits the system to be operated in two modes which might generally be called the vacuum mode in which the ion pump 20 is used and the equilibrium mode in which the high pressure ionization gauge 11 is used. It is anticipated that normally the ion pump 20 would be used because the speed of response in this mode is quite high while the equilibrium mode will require several minutes to stabilize following a change in the hydrogen concentration in the sodium.

The disclosed system may also be used to measure the hydrogen concentration in sodium vapor. The operation of the meter is substantially the same because sodium, either liquid or vapor, will not diffuse through the membrane 10.

Figure 2:
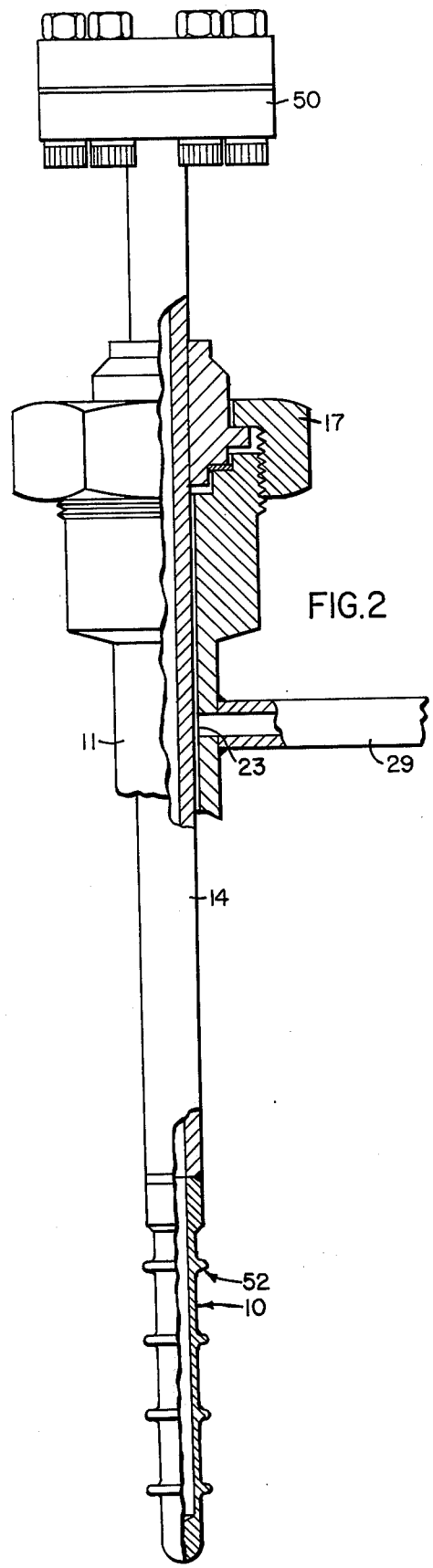
FIG. 2 is a diagram of the reinforced membrane with portions shown in cross section.

One embodiment of the membrane assembly is illustrated in FIG. 2. In this embodiment the membrane 10 is fundamentally a thin walled tube closed at one end with the wall of the tube including thicker portions which form reinforcement rings spaced along the outer surface of the tube. The membrane illustrated in FIG. 2 is preferably machined from a cast rod of a high purity nickel, e.g. 270 or 201, from stainless steel or Incoloy 800. The thin walls are also preferably about 10 mils thick with the reinforcement rings 52 spaced at distances necessary to give the membrane the proper structural strength. When the outside diameter of the membrane 10 is approximately 0.27 inches the reinforcement rings 52 can be approximately 0.37 inches in diameter and positioned from each other by 0.44 inches. This results in a membrane 10 which can be operated at differential pressures up to approximately 10 atmospheres and at temperatures up to 1000°F. The mounting tube 14 and the membrane 10 are preferably welded together using a full penetration butt weld. This may be conveniently done because when the membrane 10 is machined the upper portion can be made approximately the same thickness as the mounting tube 14.

Figure 3:
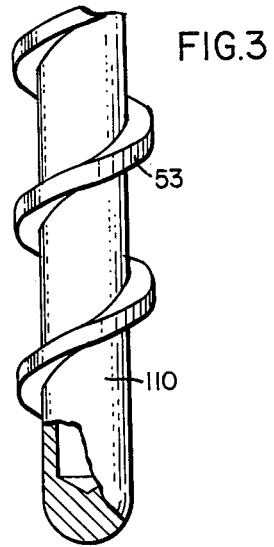
FIG. 3 is a alternate reinforced membrane illustrating a spiral reinforcement.

FIG. 3 shows a second embodiment of the membrane. This embodiment has been assigned a separate reference number to avoid confusion. In this embodiment the reinforcing rings have been replaced by a reinforcing spiral 53 which spirals around the outside portion of the membrane 110. Other types of reinforcements are also possible. For example, the reinforcing spiral 53 could be positioned on the innerwall of the membrane or combined with the ribs which are substantially parallel to the axis of the membrane and extend substantially the entire length of the membrane. Other modifications of these membranes are possible.

One salient feature of above discussed of the membranes is the fact that the membranes are formed such that the wall of the membrane includes reinforcing portions which permit the membrane walls to be substantially thinner than prior art membranes which do not utilize these reinforcing portions.

Figure 4:
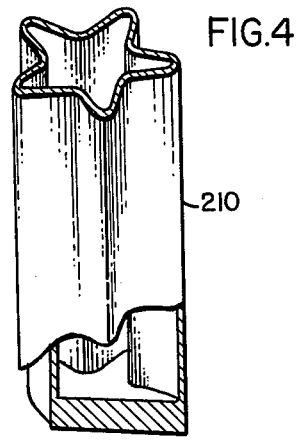
FIG. 4 is another alternate reinforced membrane illustrating how the membrane can be reinforced by selectively shaping the walls of the membrane.

Still another alternate embodiment of the membrane is illustrated in FIG. 4. This embodiment has also been assigned a separate reference numeral to avoid confusion. In this embodiment the walls of the membrane 210 have been formed such so that the cross section of the membrane is star-shaped. This configuration causes the walls of the membrane to be substantially stiffer than a tubular type membrane thereby capable of withstanding greater pressure. Other configurations not utilizing thicker reinforcement sections are also possible. For example, instead of using substantially flat portions to form a star-shaped cross section segments of a circle could be used to form a membrane having a fluted outer surface.

The disclosed hydrogen meter can be used to detect many types of system malfunctions. For example, systems which utilize liquid sodium as a heat transfer medium should have a relatively constant hydrogen concentration in the sodium. Deviation beyond expected limits can indicate a leak in the system. The leak may be contributing pure hydrogen or the hydrogen increase may be the result of water mixing with the sodium. In either case, the hydrogen concentration measurement may be useful in assuring that the system can be operated safely and in predicting when repair should be made. In order to discriminate between a hydrogen and a water leak, it may be necessary to include an oxygen meter in the system. An increase in the hydrogen concentration alone will normally indicate a hydrogen leak. An increase in the hydrogen and the oxygen indicates a water leak.

Although the above embodiments of the invention have been discussed with reference to measuring the hydrogen concentration in liquid sodium, the system is not so limited. The system may be used to measure the concentration of any gas which will preferentially diffuse through the membrane. Detectors other than the ion pump and the high pressure ionization gauge may also be used. Other modifications of the membrane and the system are also possible.

We claim:

1. A system for measuring the concentration of a gas in a flowing fluid, comprising in combination:
   a. means for diverting a small portion of said flowing fluid into a measurement loop;
   b. a membrane permeable to said gas positioned such that a portion of said gas diffuses through said membrane from said portion of said fluid which flows through said measurement loop;
c. means, responsive to said gas, for producing a signal indicative of the rate at which said gas diffuses through said membrane; and
d. means permitting said membrane to be changed without interrupting the flow of said liquid, said means including two valves for isolating said fluid in said measurement loop from the fluid in the remainder of the system and means for protecting the fluid in said measurement loop from contact with the atmosphere when said membrane is removed from said measurement loop.

2. A system in accordance with claim 1 wherein said fluid is sodium.

3. A system in accordance with claim 1 wherein said means for protecting the said fluid is a blanket of an inert gas.

4. A system in accordance with claim 3 wherein said inert gas if argon.

5. A system in accordance with claim 1 wherein said means for determining the rate at which said gas diffuses through said membrane is a high pressure ionization gauge for measuring the equilibrium pressure of said gas within said liquid.

6. A system in accordance with claim 1 wherein said means for determining the rate at which said gas diffuses through said membrane is an ion pump.

* * * * *